US010285400B2

(12) United States Patent
Lei et al.

(10) Patent No.: US 10,285,400 B2
(45) Date of Patent: May 14, 2019

(54) DISINFECTANT COMPOSITION CONTAINING QUATERNARY AMMONIUM COMPOUNDS

(71) Applicant: LONZA, INC., Allendale, NJ (US)

(72) Inventors: Deqing Lei, Alpharetta, GA (US); Philip Gerdon Sweeny, Alpharetta, GA (US)

(73) Assignee: Lonza Inc., Allendale, NJ (US)

( * ) Notice: Subject to any disclaimer, the term of this patent is extended or adjusted under 35 U.S.C. 154(b) by 109 days.

(21) Appl. No.: 14/847,108

(22) Filed: Sep. 8, 2015

(65) Prior Publication Data

US 2016/0066571 A1     Mar. 10, 2016

Related U.S. Application Data

(60) Provisional application No. 62/047,806, filed on Sep. 9, 2014.

(51) Int. Cl.
| | | |
|---|---|---|
| *A01N 33/12* | (2006.01) |
| *A01N 59/00* | (2006.01) |
| *A01N 57/20* | (2006.01) |
| *A01N 59/26* | (2006.01) |
| *A01N 37/44* | (2006.01) |
| *A01N 25/02* | (2006.01) |
| *A01N 37/04* | (2006.01) |
| *A01N 37/02* | (2006.01) |
| *A01N 41/04* | (2006.01) |

(52) U.S. Cl.
CPC ............. *A01N 33/12* (2013.01); *A01N 25/02* (2013.01); *A01N 37/02* (2013.01); *A01N 37/04* (2013.01); *A01N 37/44* (2013.01); *A01N 41/04* (2013.01); *A01N 57/20* (2013.01); *A01N 59/00* (2013.01); *A01N 59/26* (2013.01)

(58) Field of Classification Search
CPC ........ A01N 33/12; A01N 59/26; A01N 59/00; A01N 57/20; A01N 37/44; A01N 25/02; A01N 37/04; A01N 37/02; A01N 41/04
See application file for complete search history.

(56) References Cited

U.S. PATENT DOCUMENTS

| | | |
|---|---|---|
| 6,010,993 A | 1/2000 | Romano et al. |
| 6,103,683 A | 8/2000 | Romano et al. |
| 6,537,955 B1 | 3/2003 | Raso et al. |
| 6,663,860 B1 | 12/2003 | Tvedten |
| 6,689,736 B2 | 2/2004 | Thomas et al. |
| 6,762,158 B2 | 7/2004 | Lukenbach et al. |
| 6,784,145 B2 | 8/2004 | Delambre et al. |
| 6,841,090 B1 | 1/2005 | Serego et al. |
| 6,916,402 B2 | 7/2005 | Shannon et al. |
| 7,320,956 B2 | 1/2008 | Mitchell et al. |
| 7,393,528 B2 | 7/2008 | Tvedten |
| 7,462,590 B2 | 12/2008 | Tichy et al. |
| 7,511,007 B2 | 3/2009 | Tichy et al. |
| 7,553,805 B2 | 6/2009 | Tichy et al. |
| 7,670,967 B2 | 3/2010 | Runge et al. |
| 7,857,866 B2 | 6/2010 | Guerin |
| 7,833,290 B2 | 11/2010 | Guerin et al. |
| 7,879,744 B2 | 2/2011 | Seidling et al. |
| 8,138,106 B2 | 3/2012 | Hamed et al. |
| 8,277,827 B2 | 10/2012 | Toreki et al. |
| 8,304,378 B2 | 11/2012 | Baars et al. |
| 8,450,378 B2 | 5/2013 | Snyder et al. |
| 8,563,017 B2 | 10/2013 | Cunningham et al. |
| 8,574,683 B2 | 11/2013 | Hamed et al. |
| 8,642,054 B2 | 2/2014 | Green |
| 8,865,196 B2 | 10/2014 | Omidbakhsh |
| 8,926,999 B2 | 1/2015 | Toreki et al. |
| 9,226,941 B2 | 1/2016 | Cooksey |
| 2005/0100612 A1 | 5/2005 | Capps |
| 2006/0293202 A1* | 12/2006 | Cate ............. C11D 17/041 510/235 |
| 2010/0247615 A1 | 9/2010 | Toreki et al. |
| 2011/0135702 A1 | 6/2011 | Hoffman et al. |
| 2013/0037048 A1 | 2/2013 | Edgington et al. |
| 2014/0041686 A1 | 2/2014 | Ryther et al. |
| 2014/0142489 A1 | 5/2014 | Green |
| 2014/0322349 A1 | 10/2014 | Martin |
| 2014/0328941 A1 | 11/2014 | Bui et al. |

(Continued)

FOREIGN PATENT DOCUMENTS

| | | |
|---|---|---|
| EP | 1 001 012 A1 | 5/2000 |
| WO | 9400548 A1 | 1/1994 |
| WO | 0057730 A1 | 10/2000 |

(Continued)

OTHER PUBLICATIONS

Written Opinion and Search Report of PCT/US2015/014534 dated Apr. 29, 2015.
Weaver et al., "Encyclopedia of Chemical Technology, Disinfectants and Antiseptics", 3rd Ed., vol. 7, pp. 793-832.

*Primary Examiner* — Robert S Cabral
(74) *Attorney, Agent, or Firm* — McBee Moore Woodward & Vanik IP, LLC

(57) ABSTRACT

Disinfectant compositions disclosed herein comprise at least one biocidal quaternary ammonium compound, hydrogen peroxide, and optionally inorganic acid and/or organic acid. Particularly, a composition comprising a biocidal quaternary ammonium chloride compound, hydrogen peroxide, and C1 to C8 carboxylic acid, mono-, di- and tricarboxylic acid enhances significantly its antimicrobial activities of either hydrogen peroxide or the quaternary ammonium chloride alone.

21 Claims, No Drawings

(56) References Cited

U.S. PATENT DOCUMENTS

2015/0110893 A1   4/2015  Koenig et al.
2015/0196523 A1   7/2015  Raad et al.

FOREIGN PATENT DOCUMENTS

| WO | 0165939 A1      | 9/2001  |
| WO | 0170030 A2      | 9/2001  |
| WO | 03028429 A2     | 4/2003  |
| WO | 2005089100 A2   | 9/2005  |
| WO | 2011/156398 A1  | 12/2011 |
| WO | 2012/090099 A2  | 7/2012  |
| WO | 2012/090101 A2  | 7/2012  |
| WO | 2015120104 A1   | 8/2015  |

* cited by examiner

DISINFECTANT COMPOSITION CONTAINING QUATERNARY AMMONIUM COMPOUNDS

CROSS-REFERENCE TO RELATED APPLICATIONS

This application claims priority to U.S. Application No. 62/047,806, filed Sep. 9, 2014, which is herein incorporated by reference in its entirety.

BACKGROUND

1. Field

The present invention relates to a disinfecting composition comprising a biocidal quaternary ammonium compound and hydrogen peroxide. An embodiment of the composition comprises a biocidal quaternary ammonium chloride compound in a hydrogen peroxide/water solution. In addition, the composition can further comprise an acid. The disclosure also provides methods of using the same to kill or inhibit the growth of microorganisms, such as bacteria, viruses, fungi, mildew, and mold. The disclosure also provides for methods of disinfecting surfaces, such as a hard surface, comprising applying a disinfecting composition of the invention to the surface.

2. Description of Related Art

Pathogenic organisms, such as bacteria, fungi, and viruses, continue to cause infections in humans as well as domestic animals and pets. In recent years, there has been a particular growing concern over food-borne pathogens and the potential for them to contaminate the food chain. Disinfectant formulations have been developed over the last several decades to reduce or destroy pathogenic organisms and accordingly, reduce the rate of infection. Literally any hard surface including floors, walls, countertops, windows, windowsills, sinks, faucets, waste containers, appliances, and cabinet surfaces can become contaminated. Disinfectants have been developed to treat hard surfaces for use in hospitals, rest homes, schools, and homes.

The use of quaternary ammonium compounds (quats) as biocides is well known (See e.g. Kirt-Othmer's Encyclopedia of Chemical technology, $3^{rd}$ Ed., Vol. 7, pp. 793-832, in particular pp. 815-818).

However, quaternary ammonium compounds (i.e., dialkyl quaternary ammonium compound (DDAC) and Dodecyl Dimethyl Benzyl Ammonium Chloride (ADBAC)), while inexpensive and effective biocides, have limitations. For example, when exposed to hard water, efficacy is severely reduced. To compensate, the use of chelants are usually required to sequester water insoluble cations.

The typical quaternary ammonium compound utilizes chloride as the anionic counterion, which when in the presence of metals such as steel, tin, and aluminum can cause corrosion. To compensate, the use of corrosion inhibitors is sometimes necessary.

Proposed quantified standardized methods that will be used to evaluate and support antimicrobial activity have shown to demonstrate bias at various levels for quat-containing formulas.

Didecyl dimethyl ammonium carbonate/bicarbonate compound (DDABC) does help mitigate (but not totally eliminate) hard water and corrosion issues as described above. However, there are still limiting factors even with this compound. While most chloride-containing quats are stable across much of the pH scale, DDABC is limited to alkaline systems. If attempts are made to utilize the DDABC molecule in neutral or acid systems, the carbonate/bicarbonate reacts, which undesirably releases carbon dioxide gas.

Thus, there is a need for compositions with improved efficacy against microorganisms.

A solution to this technical problem is provided by the embodiments characterized in the claims.

BRIEF SUMMARY

In an aspect, the disclosure provides for a disinfecting composition comprising a biocidal quaternary ammonium compound and hydrogen peroxide with improved anti-microbial efficiency. An embodiment of the composition comprises a biocidal quaternary ammonium chloride compound in a hydrogen peroxide/water solution. In addition, the composition can further comprise an acid.

In an aspect, the disclosure provides for a biocidal quaternary ammonium chloride compound with improved antimicrobial efficiency.

In an aspect, the disclosure provides for another disinfecting composition comprising quaternary ammonium chloride compound, an acid, and hydrogen peroxide with improved efficacy against microorganisms.

In an aspect, the quaternary ammonium chloride compound comprises didecyl dimethyl ammonium chloride and/or $C_8$-$C_{18}$ alkyldimethylbenzylammonium chloride.

In an aspect, the acid comprises phosphoric acid. In other aspects, the acid comprises one or more of $C_1$-$C_8$ organic acid(s), mono-, di- and tri-carboxylic acid, and hydroxylacid such as acetic, phosphoric, tartaric, adipic acid, oxalic acid, sulfamic acid, succinic acid, lactic acid, glutaric acid, benzoic acid, polymeric acid such as poly(co-acrylic-maleic acid), formic acid, citric acid, glycolic acid, and a mixture thereof.

In an aspect, the disclosure also provides for a method of using the same.

The disclosure also provides for a method of disinfecting surfaces, preferably a hard surface, comprising applying a disinfecting composition of the invention to the surface.

In an aspect, the novel disinfecting composition and novel disinfecting active has improved efficacy against *Pseudomonas aeruginosa* and *Staphylococcus aureus*, and *Mycobacterium terrae*.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

The subject disclosure features, in one aspect, a disinfecting composition comprising a quaternary ammonium chloride compound and hydrogen peroxide with improved antimicrobial efficiency. An embodiment of the composition comprises a quaternary ammonium chloride compound in a hydrogen peroxide/water solution. In addition, the composition can further comprise an acid. In an additional embodiment, the composition consists essentially of a quaternary ammonium chloride compound, hydrogen peroxide, and an acid. In another embodiment the composition consists of a quaternary ammonium chloride compound, hydrogen peroxide, and an acid.

In an aspect, the disclosure provides for a quaternary ammonium chloride compound with improved anti-microbial efficiency. In an aspects, the combination of the quaternary ammonium chloride, the hydrogen peroxide, and the optional acid act synergistically.

Quaternary ammonium compounds useful in the present invention include, but are not limited to, those having the formula (I):

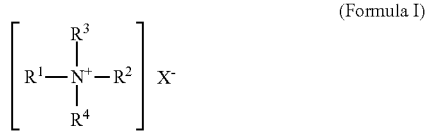

(Formula I)

wherein $R^1$ is a benzyl group, a $C_1$-$C_{22}$ alkyl or an optionally aryl substituted alkyl group;

$R^2$ and $R^3$ are independently optionally substituted $C_1$-$C_{22}$ alkyl groups;

$R^4$ is selected from the group consisting of a $C_1$-$C_{22}$ alkyl or aryl-substituted alkyl group, benzyl group, and —[$(CH_2)_2$—O]$_n$—$R^5$, wherein n is an integer from 1 to 20 and $R^5$ is selected from the group consisting of hydrogen, phenyl, alkyl, and alkyl-substituted phenyl;

and $X^-$ is chlorine, bromine, and phosphate and sulfate and nitrate.

In an aspect, $R^1$ is a substituted benzyl group or a $C_{1-22}$ alkyl or aryl-substituted alkyl group.

In an aspect, $R^4$ is selected from the group consisting of $C_{1-20}$ alkyl or aryl-substituted alkyl group, benzyl group, and —[$(CH_2)_2$—O]$_n$—$R^5$, wherein n is an integer from 1 to 20 and $R^5$ is selected from the group consisting of hydrogen, phenyl, alkyl and alkyl-substituted phenyl.

In an aspect, $R^1$ and $R^4$ are the same benzyl groups or $C_{1-22}$ alkyl or aryl-substituted alkyl groups.

In an aspect, $R^1$ and $R^4$ are $C_{1-22}$ alkyl.

In an aspect, $R^1$ and $R^4$ are $C_{10}$ alkyl, preferably n-decyl.

In an aspect, $R^2$ and $R^3$ are independently $C_{1-22}$ alkyl.

In an aspect, $R^2$ and $R^3$ are the same $C_{1-22}$ alkyl groups. In an aspect, $R^2$ and $R^3$ are $C_1$-$C_4$ alkyl. In an aspect, $R^2$ and $R^3$ are methyl.

Here and below the expression "$C_{1-22}$ alkyl" is to be understood to comprise methyl, ethyl, and all linear or branched alkyl groups having 3 to 22 carbon atoms. Accordingly, the expression "$C_{3-22}$ alkyl" is to be understood to comprise all linear or branched alkyl groups having 3 to 22 carbon atoms.

The term "aryl-substituted alkyl group" refers to hydrogen atom(s) of an alkyl group substituted by one or more aromatic carbon rings. Similarly, the term "aryl-substituted $C_{1-22}$ alkyl group" refers to hydrogen atom(s) of $C_1$-$C_{22}$ alkyl group substituted by one or more aromatic carbon rings.

The expression "alkyl-substituted phenyl" is to be understood to comprise any phenyl group bearing from one to five alkyl groups, in particular $C_{1-20}$ and preferably $C_{1-8}$ alkyl groups as substituents.

In an embodiment of the invention, the composition is a concentrated solution that can be diluted with water to a ready-to-use solution.

In an embodiment, the concentrated composition comprises about 0.1% to about 25% by weight of one or more quaternary ammonium compounds. In another embodiment, the concentrated composition comprises about 0.5 to about 10% by weight of one or more quaternary ammonium compounds. In a particular embodiment, the concentrated composition comprises about 1% to about 8% by weight of one or more quaternary ammonium compounds. In a preferred embodiment, the concentrated composition comprises about 2% to about 5% by weight of one or more quaternary ammonium compounds.

In an additional embodiment, the ready-to-use composition comprises about 0.01% to about 2.5% by weight of one or more quaternary ammonium compounds. In a further embodiment, the ready-to-use composition comprises about 0.03% to about 2% by weight of one or more quaternary ammonium compounds, preferably 0.1% to 1.5% by weight of one or more quaternary ammonium compounds.

In an aspect, the concentrated composition may include from about 0.5% by weight to about 25% by weight of hydrogen peroxide. In another aspect, the concentrated composition may include from about 1% by weight to about 10% by weight of hydrogen peroxide. In a preferred aspect, the concentrated composition may include about 3% by weight to about 8% by weight of hydrogen peroxide.

In an additional aspect, the ready-to-use composition may include from about 0.01% by weight to about 5% by weight of hydrogen peroxide. In a further embodiment, the ready-to-use composition may include from about 0.06% by weight to about 2% by weight of hydrogen peroxide. In a preferred aspect, the ready-to-use composition may include about 0.1% by weight to about 1.5% by weight of hydrogen peroxide.

In an embodiment of the invention, the compositions comprise at least one acid or salt thereof. The acid may be an inorganic acid or an organic acid. In a preferred embodiment the acid is a C1 to C8 carboxylic acid. In a more preferred embodiment, the acid is a monocarboxylic acid, a dicarboxylic acid, a tricarboxylic acid, or a mixture thereof. In an additional embodiment, the acid is a hydroxyacid, an aromatic acid, or a mixture thereof. In another additional embodiment, the acid is methanesulfonic acid, phosphoric acid, etidronic acid, phytic acid, phosphoacetic acid, N-(phosphonomethyl)iminodiacetic acid, diethylenetriaminepentakis(methylphosphonoic acid), S,S-ethylenediamine-N'N'-disuccinic acid, their alkaline salts, or any mixture thereof.

In some embodiments, the acid is citric acid, phosphoric acid, succinic acid, lactic acid, S,S-ethylenediamine-N,N'-disuccinic acid, 1-hydroxyethane 1,1-diphosphonic acid (HEDP), dipicolinic acid (DPA), methanesulfonic acid (MSA), their alkaline salts, or any mixture thereof.

In a preferred embodiment, the acid is a mixture of acids. In some embodiments, the acid comprises one or more of the following organic acids: citric acid, succinic acid, phosphoric acid, and lactic acid. In another embodiment, the acid comprises one or more of the following acids: citric acid, succinic acid, phosphoric acid, and lactic acid, in combination with another acid. For example, citric acid may be used in combination with ethylenediamine-N,N'-disuccinic acid or its alkaline salt, HEDP, and/or MSA. As another example, succinic acid may be used in combination with ethylenediamine-N,N'-disuccinic acid or its alkaline salt, HEDP, and/or MSA. As another example, phosphoric acid may be used in combination with ethylenediamine-N,N'-disuccinic acid or its alkaline salt, HEDP, and/or MSA. As another example, lactic acid may be used in combination with ethylenediamine-N,N'-disuccinic acid or its alkaline salt, HEDP, and/or MSA.

In an aspect, the concentrated composition may include from about 0.01% by weight to about 25% by weight of the acid or mixture of acids. In a particular concentrated composition, there may include from about 0.05% by weight to about 14% by weight of the acid or mixture of acids. In a preferred aspect, the concentrated composition may include from about 1% by weight to about 5% by weight of the acid or mixture of acids.

In an additional aspect, the ready-to-use composition may include from about 0.01% by weight to about 10% by weight of the acid or mixture of acids. In another aspect, the ready-to-use composition may include from about 0.05% by weight to about 6% by weight of the acid or mixture of acids. More preferably, the ready to use composition may include from about 0.5 to about 4% by weight of the acid or mixture of acids.

In another aspect, the ready-to-use composition may include from about 1% by weight to about 5% by weight of an organic acid such as citric acid, succinic acid, phosphoric acid, lactic acid, or any mixture thereof. In a preferred aspect, the ready-to-use composition may include from about 2% by weight to about 4% by weight of an organic acid such as citric acid, succinic acid, phosphoric acid, lactic acid, or any mixture thereof.

In an additional aspect, the ready-to-use composition may include from about 1% by weight to about 5% by weight of an organic acid such as citric acid, succinic acid, phosphoric acid, lactic acid, or any mixture thereof, in combination with another acid. In another aspect, the ready-to-use composition may include from about 1% by weight to about 5% by weight of an organic acid such as citric acid, succinic acid, phosphoric acid, lactic acid, or any mixture thereof, in combination with from about 0.05% by weight to about 5% by weight of another acid. In a preferred aspect, the ready-to-use composition may include from about 2% by weight to about 4% by weight of an organic acid such as citric acid, succinic acid, phosphoric acid, lactic acid, or any mixture thereof, in combination with from about 0.1% by weight to about 4% by weight of another acid such as ethylenediamine-N,N'-disuccinic acid or its alkaline salt, HEDP, and/or MSA.

The composition can be made in any desired manner. For example, the ingredients can be mixed in any order. Without being limiting, one of the methods to make the disinfecting composition comprises mixing a quaternary ammonium chloride with an acid (either a mineral or organic) prior to hydrogen peroxide addition. The hydrogen peroxide may optionally be provided to the end user separate from the quaternary ammonium compound and acid. That is the composition may be provided as a two-part composition to the end user and the end user mixes the two parts together. In addition, the end user may also add additional water to the composition to adjust the composition to the ready to use compositions.

In an aspect, the disclosure also provides for a method of using the compositions to kill or to inhibit the growth of microorganisms. In an aspect, the quaternary ammonium compound, hydrogen peroxide, and optionally at least one acid, of the composition are applied together. In an aspect, the quaternary ammonium compound, hydrogen peroxide, and optionally at least one acid, of the composition are applied separately.

In an aspect, the compositions have improved microbial efficacy against a variety of microorganisms that are potentially harmful or capable of causing disease, such as Gram positive and Gram negative bacteria, viruses, fungi, mildew, and mold. Such microorganisms comprise *Staphylococcus, Pseudomonas*, hepatitis, rotavirus, rhinovirus, and *Mycobacterium terrae*. In an aspect, the compositions has improved microbial efficacy against *S. aureus, E. coli, Candida albicans, Aspergillus niger*, and *P. aeruginosa*, especially *Mycobacterium terrae*.

Suitable methods of determining an increase in biocidal efficacy are known in the art. Biocidal efficacy can be measured as an increase in percentage kill for a biocidal target after a specified time in contact with the composition (e.g. efficacy percentage). The EPA has regulations regarding required contact times for different surfaces and also accepted regulatory protocols for testing, which are known to one skilled in the art. In another embodiment, the increased biocidal efficacy can be measured as a decrease in the kill time of a composition, e.g. the amount of time necessary to kill at least 99.9% of the biocidal target on a surface after a specified contact time. The EPA-approved and industrial standard contact time for a bucket dilutable composition using a use dilution test for major biocidal targets, e.g. *Staphylococcus aureus, Salmonella enterica*, and *Pseudomonas aeruginosa*, etc., is 10 minutes.

There exists a need for shorter contact times of disinfectant compositions with, for example, a work surface to approximate real world use of these compositions. Thus, determined by OECD Quantitative Method for Evaluating Bacterial Activity of Microbiocides Used on Hard Non-Porous Surfaces, the compositions of the invention can have a microbial contact kill time of less than about 10 minutes, preferably a microbial contact kill time of less than about 5 minutes. In a more preferred embodiment, the compositions of the invention have a microbial contact kill time of about 3 minutes or less, alternatively about 2 minutes or less, alternatively about 1 minute or less, alternatively about 30 seconds or less.

In an additional embodiment, the compositions of the invention demonstrate a minimum of 4 log reduction in the number of microorganisms within about 5 minutes of contact time. In a preferred embodiment, the compositions of the invention demonstrate a minimum of 4 log reduction in the number of microorganisms within about 3 minutes of contact time, alternatively within about 2 minutes of contact time, alternatively within about 1 minute of contact time, alternatively within about 30 seconds of contact time.

In an additional embodiment, the compositions of the invention demonstrate a minimum of 5 log reduction in the number of microorganisms within about 5 minutes of contact time. In a preferred embodiment, the compositions of the invention demonstrate a minimum of 5 log reduction in the number of microorganisms within about 3 minutes of contact time, alternatively within about 2 minutes of contact time, alternatively within about 1 minute of contact time, alternatively within about 30 seconds of contact time.

Unexpectedly, the compositions disclosed herein comprising a quaternary ammonium chloride compound, hydrogen peroxide, and an acid, such as a composition of Examples 5-7 described below, demonstrated greater than 5 log reduction in *Staphylococcus aureus* and *Pseudomonas aeruginosa*, two major biocidal targets, within 3 minutes of contact time. Additionally, the ready-to-use compositions disclosed herein comprising a quaternary ammonium chloride compound, hydrogen peroxide, and an acid diluted in hard water, such as a composition of Examples 8-11 described below, demonstrated greater than 5 log reduction in *Staphylococcus aureus* and *Pseudomonas aeruginosa* within 1 minute of contact time. Increasing the concentration of hydrogen peroxide to 1% in the ready-to-use composition, such as the composition of Example 11 described below, resulted in a surprising greater than 5 log reduction in *Staphylococcus aureus* and *Pseudomonas aeruginosa* within 30 seconds of contact time.

The storage stable compositions of the invention also have a pH which maintains the shelf life stability of the compositions, and in particular, maintains the stability of the hydrogen peroxide, so oxygen is not readily released from solution. The compositions of the invention have been demonstrated to remain stable for four weeks in a 45° C. temperature controlled oven, which is equivalent to one year storage shelf life under normal storage conditions. The concentrated compositions of the invention have a pH from about 1.6 to about 5. The ready-to-use compositions of the invention have a pH from about 1.8 to about 6.

In another embodiment, the concentrate and ready-to-use solution of the may further include a stabilizer to deactivate impurities that can cause hydrogen peroxide decomposition. The stabilizer may be added to prevent the components from decomposing on the shelf prematurely during storage of the formulations. Stabilizers for use in stabilizing acidic hydrogen peroxide solutions include organic and inorganic sequestering agents, i.e., stannates and phosphates, and combinations of organic compounds, organometallic salts and metal chelators with or without stannates and phosphates. In one embodiment, the stabilizer may be phosphoric acid, a derivative of phosphoric acid, 1-hydroxyethylidene-diphosphonic acid (HEDP), phytic acid, aminophosphate, phosphonate and sodium glutamate, NaH2PO4, Na tripolyphosphate, organophosphonic acid, amino-phosphonate, silver dihydrogen citrate, diphosphonic acid, ethylenediaminetetraacetic acid (EDTA), N-(hydroxyethyl)-ethylenediaminetriacetic acid (HEDTA), tri(methylene phosphoric acid), diethylenetriaminepenta(methylene phosphoric acid), 2-hydroxy ethylimino bis(ethylene phosphoric acid), citric acid, dipicolinic acid, ethylenediamine-N,N'-disuccinic acid, methylglycinediacetic acid and their alkaline salts thereof, nitriotriacetic acid (NTA), 2-hydroxyethylimino-diacetic acid (HEIDA), and salts thereof, cyclohexane-1,2-diaminotetrakismethylene phosphonic acid or water-sol, diethylenetriamine penta(methylene phosphonic acid), colloidal stannate, diethylenetriamine pentaacetic acid (DTPA), citrate salts, gallate salts, malate salts, malonate salts, oxaloacetate salts, oxalate salts, pyruvate salts, succinate salts, or mixtures thereof. The hydrogen peroxide stabilizer can be a single component or a mixture of the derivatives of phosphoric acid and the chelators described above. The amount of the optional stabilizer in the concentrate can be from about 0.01% to about 5 w/w %, preferably from 0.05% to 2 w/w %, and more preferably from 0.1% to 1.0 w/w %. In other embodiments, stabilizers are not present.

The disclosure also provides for a method of disinfecting a surface comprising applying the compositions or quaternary ammonium chloride compound to the surface. In an aspect, the quaternary ammonium compound, hydrogen peroxide, and optionally the acid, of the composition are applied together. In an aspect, the quaternary ammonium compound, hydrogen peroxide, and optionally the acid, of the composition are applied separately.

In one embodiment, the disinfecting compositions further comprise a solvent. In one embodiment, the solvent may be water. In another embodiment, the solvent may be mixtures of ethanol, propanol, propylene glycol, isopropanol, or other alcohols. In another embodiment, the solvent may be mixtures of ethanol, propanol, isopropanol, and/or alkyl and dialklyl glycol ethers of ethylene glycol or propylene glycol, such as diethylene glycol propyl ether, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, DEG monobutyl ether, diethylene glycol monoethyl ether, diethylene glycol mono-n-butyl ether, ethylene glycol dimethyl ether, ethylene glycol diethyl ether, ethylene glycol dibutyl ether, propylene glycol n-butyl ether, dipropylene glycol n-propyl ether, tripropylene glycol methyl ether, dipropylene glycol methyl ether, and dipropylene glycol butyl ether. In another embodiment, the solvent may be glycol ethers, non-ionic and amphoteric surfactants and chelants. For example, the glycol ether may be DOWANOL™ DPnP glycol ether. The amount of the solvent in the composition can be from about 0.5% to about 20 w/w %, preferably from about 1% to about 5 w/w %. In other embodiments, solvents are not present.

Optionally, a surfactant may be added as well to the disinfecting compositions. Suitable surfactants include, but are not limited to, amphoteric, surfactants, zwitterionic surfactants, or non-ionic surfactants, for example, amine oxides, linear alcohol ethoxylate, secondary alcohol ethoxylates, ethoxylate esters, betamines, and alkyl polyglycerides. For example, the surfactant may be STEPANETEX® DA-6. In other embodiments, surfactants are not present.

The compositions of the invention can also include additives, such as chelators, builder salts, dyes, fragrances, hydrogen peroxide stabilizers, corrosion inhibitors, antifoam agents, pH buffers, pH adjustment agents, nonionic surfactants, wetting agents, and perfluorosurfactants, such as those commonly used in the art of cleaning and disinfecting solutions. The compositions of the invention can also include additives such as a leveling agent, such as those commonly used in the art of coatings or paints. The compositions can also be free of chelants. The composition can also be free of one or more of builder salts, dyes, fragrances, hydrogen peroxide stabilizers, corrosion inhibitors, antifoam agents, pH buffers, pH adjustment agents, nonionic surfactants, wetting agents, perfluorosurfactants and leveling agents.

In some embodiments, the compositions of the invention further comprise a chelator and/or a corrosion inhibitor. Any known chelator or corrosion inhibitors can be used. The compositions can also be free of chelators and/or corrosion inhibitors.

The disclosure also provides for a disinfecting composition that does not comprise a cationic polymer. The cationic polymers preferably excluded from the composition may have the following structure:

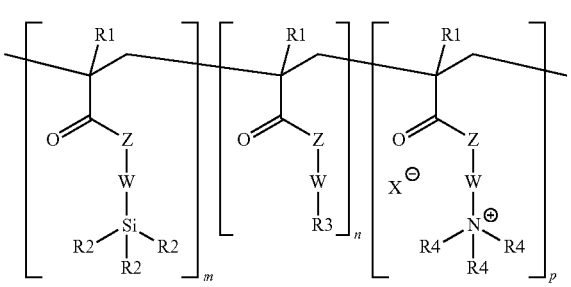

With respect to this structure, R1 may be independently selected from H (hydrogen) or methyl (CH3); R2 may be independently selected from H (hydrogen), halide (fluoride, chloride, bromide, iodide), C1 through C6 alkyl or alkoxy, aryl, linear or branched oligomeric or polymeric dimethyl siloxane; R3 may be independently selected from hydroxyl, alkyl amine, dialkyl amine or polyether; R4 may be independently selected from H (hydrogen), C1 through C6 alkyl, or benzyl; Z may be independently selected from O (oxygen) or NH; W may be independently selected from C1 through C6 alkyl; and X may be independently selected from fluoride, chloride, bromide, iodide, methosulfate or ethosulfate. Alternatively, the monomer represented by subscript "n" may be a vinyl pyrrolidinone. The values of m, n and p may be the same or they may be different. The values of m, n and p are integers and are selected to make the number average molecular weight in the range of 1000 to 100,000 g/mol.

In one aspect, examples of cationic polymers preferably excluded from the composition include cationic polymers that include a (3-acrylamidopropyl)trimethylammonium chloride monomer combined with another monomer selected from a group consisting of a polar, water-soluble monomer, a hydrophobic, silicone-containing monomer and mixtures of such monomers. The polar, water-soluble monomer may be selected from vinyl pyrrolidinone, hydroxyl ethyl acrylate, hydroxyl ethyl methacrylate, N,N'-dimethyl acrylamide, acrylamide and N-isopropyl acrylamide. The hydrophobic, silicone-containing monomer may be selected from unsubstituted or substituted vinyl or ethynyl group terminated siloxyl compounds, comprising monomethacryloxypropyl terminated polydimethylsiloxane, methacryloxypropyl tris(trimethylsiloxysilane) and methacryloxypropyl terminated T-structure siloxane.

In another aspect, examples of cationic polymers preferably excluded from the composition include cationic polymers that include a [2-acryloyloxy)ethyl]trimethylammonium chloride monomer combined with another monomer selected from a group consisting of a polar, water-soluble monomer, a hydrophobic, silicone-containing monomer and mixtures of such monomers. The polar, water-soluble monomer may be selected from vinyl pyrrolidinone, hydroxyl ethyl acrylate, hydroxyl ethyl methacrylate, N,N'-dimethyl acrylamide, acrylamide and N-isopropyl acrylamide. The hydrophobic, silicone-containing monomer may be selected from unsubstituted or substituted vinyl or ethynyl group terminated siloxyl compounds, comprising monomethacryloxypropyl terminated polydimethylsiloxane, methacryloxypropyl tris(trimethylsiloxysilane) and methacryloxypropyl terminated T-structure siloxane.

According to WO 2012/090100, the cationic polymers are indicated to provide a durable or persistent activity to kill and prevent the growth of potentially-harmful microorganisms. The cationic polymers of WO 2012/090100 are preferably not present in the compositions of the present invention.

Suitable surfaces include, but are not limited to hard surfaces or food containers. In an aspect, the surface is a hard surface. In a further embodiment, the hard surface is any hard surface found in the home or an industrial or institutional setting. In another embodiment, the hard surface is a floor, wall, countertop, appliance, or fixture.

Surfaces, which may be disinfected with the compositions include, but are not limited to, those located in dairies, homes, health care facilities, swimming pools, canneries, food processing plants, restaurants, hospitals, institutions, and industry, including secondary oil recovery. Hard surfaces, such as glass and polished aluminum, are particularly suited for application. Specific areas targeted for application include hard surfaces in the home such as kitchen countertops, cabinets, appliances, waste cans, laundry areas, garbage pails, bathroom fixtures, toilets, water tanks, faucets, mirrors, vanities, tubs, and showers. The compositions can also be used to sanitize floors, walls, furniture, mirrors, toilet fixtures, windows, and wood surfaces, such as fence rails, porch rails, decks, roofing, siding, window frames, and door frames. The compositions, quaternary ammonium chloride compound, and disinfecting active are particularly well suited for application on indirect food contact surfaces, such as cutting boards, utensils, containers, dishes, wash basins, appliances, and countertops. The compositions or quaternary ammonium chloride compound can be used to sanitize diary plant equipment, milking machines, milk pails, tank trucks, and the like. Areas in hospitals would include beds, gurneys, tables, canisters, toilets, waste cans, stands, cabinets, shower stalls, floors, walls or any other non-porous surface.

The amount of compositions used to treat a surface is a biocidal effective amount, i.e. that amount to sanitize or disinfect the surface. The biocidal effective amount will depend upon the use intended and can be determined by one of ordinary skill in the art in light of the present detailed disclosure.

Typically, the disinfectant compositions can either be supplied in a dilutable concentrated form or in a ready-to-use form. A typical dilutable concentrate will comprise from about 2% by weight to about 5% by weight of quaternary ammonium compounds, about 3% to about 8% hydrogen peroxide, and about 1% to about 5% by weight of the acid based upon 100% by weight of total composition. Dilutable concentrates of the invention may be dilutable with water. A typical ready to use formulation will comprise from about from 10 ppm to about 10,000 ppm of quaternary ammonium compounds, about 0.1% to about 1.5% by weight of hydrogen peroxide, and about 0.5% to about 4% by weight of the acid based upon total composition. Water is added to achieve the desired ppm of the components.

Treatment of the surface is accomplished by any means known to those of ordinary skill in the art including, but not limited to, dipping, soaking, brushing, spraying, mopping, washing, or the like. The length of treatment required will vary according to treatment conditions, the selection of which is known to those skilled in the art.

One particularly useful application method is to impregnate the disinfecting composition comprising the quaternary ammonium chloride compound, hydrogen peroxide, and optionally, an acid, into a wipe substrate. In this embodiment, the wipe is a single use wipe that is impregnated with the disinfecting composition and is stored in a container that will dispense the wipe to a user. The container with the wipes may contain a single wipe, or several wipes. Suitable containers include a pouch containing a single wipe, such as a moist towelette which is torn open by the user, or may be a pouch with a resealable opening containing several wipes in a stacked fashion, a rolled fashion or other suitable formation that would allow a single wipe to be removed from the opening at a time. Pouches are generally prepared form a fluid impervious material, such as a film, a coated paper or foil or other similar fluid impervious materials. In another way to dispense wipes of the present invention is to place the wipe in to a fluid impervious container having an opening to access the wipes in the container. Containers may be molded plastic container with lids that are fluid impervious. Generally, the lid will have an opening to access the wipes in the container. The wipe in the container may be in a interleaved stacked, such that as a wipe is removed from the container the next wipe is positioned in the opening of the container ready for the user to remove the next wipe. Alternatively, the wipe may be a continuous material which is perforated between the individual wipes of the continuous material. The continuous wipe material with perforations may be in a folded form or may be in a rolled form. Generally, in the rolled form, the wipe material is feed from the center of the rolled material. As with the interleaved stack, as a wipe is removed from the container, the next wipe is positioned in the opening for the use to remove the next wipe, when needed.

Disposable wipes provide advantages over other application vehicles, such as a reusable sponge, rag or the like. Unlike sponges, rags and the like, which are used repeatedly, the impregnated wipe is used a single time and disposed of. As is mentioned above, reused sponge or rag presents problems since the sponge or rags may carry microbes that are not easily killed by the disinfecting composition. Further, the disinfecting composition is formulated to treat hard surface, not porous soft surfaces that are present in sponges or rags.

The disinfecting composition can be impregnated into the wipe such that the wipe is pre-moistened and will express or release the disinfecting composition on to the surface as the wipe is run across the surface to be treated. Generally, the disinfecting composition is saturated into the wipe such that the wipe will release the disinfecting composition to the surface through the wiping action. Depending on the wipe substrate, saturation was generally achieved using about 3 wt parts of the use disinfecting composition per 1 wt part of the wipe substrate to be saturated. Generally, the disinfecting composition is used from about 4 parts to 6 parts by weight per 1 part by of the wiper substrate. In these ranges, complete saturation of the substrates can be achieved. It is noted that the amount of the disinfecting solution may go up or down to achieve complete saturation of the wipe substrate, depending on the particular wipe substrate.

Suitable wipe substrates include woven and nonwoven materials. Essentially any nonwoven web material may be used. Exemplary nonwoven materials may include, but are not limited to meltblown, coform, spunbond, airlaid, hydroentangled nonwovens, spunlace, bonded carded webs, and laminates thereof. Optionally, the nonwoven may be laminated with a film material as well. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter or more.

In one embodiment the wipe is impregnated with a liquid component containing both active and inert ingredients within the allowable tolerance levels and the disinfecting composition expressed from the wipe contains active ingredients within the allowable tolerance levels. Once applied to the surface, the antimicrobial disinfecting composition is allowed to remain on the surface for a period of time. The antimicrobial composition may be applied to the surface and allowed to dry or may alternatively be dried by wiping the surface with a dry wipe or wiping device, which is preferably unused.

The following examples serve to illustrate certain aspects of the disclosure and are not intended to limit the disclosure.

EXAMPLES

Example 1: Biocidal Activities Against *Staphylococcus aureus* and *Pseudomonas aeruginosa*

Biocidal activities of the exemplified compositions were determined using OECD Quantitative Method for Evaluating Bacterial Activity of Microbiocides Used on Hard Non-Porous Surfaces.

The raw materials, 50% hydrogen peroxide, citric acid (CA), 85% phosphoric acid, glutaric acid (GA), 50% 1-hydroxyethane 1,1-diphosphonic acid (HEDP), sodium stannate, dipicolinic acid (DPA) and S,S-ethylenediamine-N,N'-disuccinic acid trisodium salt (EDDS) were purchased from Aldrich-Sigma. Bardac 2250, containing of 50% didecyldimethylammonium chloride and 10% ethanol from Lonza, was used for the formulations.

The results shown in Table 1 demonstrate the antimicrobial efficacy of the compositions when exposed to *Staphylococcus aureus* (Sa) and *Pseudomonas aeruginosa* (Pa). The compositions listed in Table 1 were tested by diluting the samples with 375 ppm hard water to test the level of hydrogen peroxide calculated based on the amount of hydrogen peroxide used to produce the compositions.

The results demonstrate that both hydrogen peroxide and Bardac 22 alone are ineffective against both Sa and Pa within 5 min of contact time. As shown in samples 1 and 2, treatment with 0.5% and 6% hydrogen peroxide alone achieved only <1.6 and <3.2 log reduction against Pa and Sa, respectively after 5 min of contact time. As sample 3 shows, treatment with 5000 ppm of Bardac 22 alone resulted in <3.3 log reduction against Pa and Sa after 5 min of contact time.

However, the combination of 3000 ppm of hydrogen peroxide and 2000 ppm of Bardac 22 as shown in sample 4, greater than 4 log reduction was achieved against Pa and Sa within 5 min of contact time.

TABLE 1

| Sample ID | Test composition | # Log Reduc. 5 min contact | |
|---|---|---|---|
| | | Pa | Sa |
| 1 | 0.5% $H_2O_2$ | 1.6 | 0.3 |
| 2 | 6.0% $H_2O_2$ | 1.8 | 3.2 |
| 3 | 5000 ppm Bardac 22 | 3.3 | 2.2 |
| 4 | 2000 ppm Bardac 22 + 3000 ppm $H_2O_2$ | 4.2 | 4.4 |

Bardac 22: didecyldimethylammonium chloride

The results shown in Table 2 further demonstrate that the disclosed compositions comprising of didecyldimethylammonium chloride, hydrogen peroxide, and phosphoric acid and/or organic phosphonic acid such as HEDP show significant synergy enhancement of antimicrobial activities against both Pa and Sa. For example, samples 5 and 6 demonstrate that both compositions at 0.5% $H_2O$, and 0.3% Bardac 22 level achieved greater than 5 log reduction against Pa and Sa within 3 min of contact time. Also, both compositions containing 0.1% $H_2O$, and 0.06% Bardac 22 achieved greater than 5 log reduction within 10 min of contact time against both Pa and Sa.

The results further demonstrate that the compositions containing an additional organic acid provide further enhancement of antimicrobial activities as shown in samples 7, 8, 9, 10 and 11. Particularly, the formulation comprising 0.5% $H_2O$, and 0.3% Bardac 22 and 1.5% citric acid in sample 8 achieved >5 log reduction against both Pa and Sa within 1 min of contact time. More particularly, the composition 11 comprising of 1.0% hydrogen peroxide achieved >5 Log reduction against Pa and Sa within only 30 seconds of contact time. In comparison, the same formulation without citric acid as shown in sample 5 achieved only <1.6 log reduction against Pa and Sa within one minute of contact time.

didecyldimethylammonium chloride and 10% ethanol from Lonza, was used for the formulations.

The results shown in Table 3 demonstrate the antimicrobial efficacy of the compositions when exposed to *Bacillus subtillis*. The compositions listed in Table 3 were tested by diluting the samples with deionized water to test the level of hydrogen peroxide calculated based on the amount of hydrogen peroxide used to produce the compositions.

TABLE 2

| Sample ID | Composition | # Log Reduc. 1 min contact 0.5% $H_2O_2$ | | # Log Reduc. 30 seconds contact 1.0% $H_2O_2$ | | # Log Reduc. 3 min contact 0.5% $H_2O_2$ | | # Log Reduc. 10 min contact 0.1% $H_2O_2$ | |
|---|---|---|---|---|---|---|---|---|---|
| | | Pa | Sa | Pa | Sa | Pa | Sa | Pa | Sa |
| 5 | 5% $H_2O_2$ + 3.0% Bardac 22 + 1.96% PA + 0.25% HEDP (pH: 1.9) | 1.6 | 1.0 | | | 5.6 | 6.0 | >5 | >5 |
| 6 | 5.0% $H_2O_2$ + 3.0% Bardac 22 + 0.19% HEDP (pH: 2.1) | | | | | 5.6 | 6.0 | >5 | >5 |
| 7 | 5% $H_2O_2$ + 3% CA + 3% Bardac 22 + 1% PA (pH: 1.5) | | | | | 6.4 | 6.1 | | |
| 8 | 1.0% $H_2O_2$ + 3% CA + 0.6% Bardac 22 + 0.4% PA (pH: 1.9) | 5.7 | 5.1 | | | | | | |
| 9 | 1.0% $H_2O_2$ + 2% CA + 1.0% Bardac 22 + 0.4% PA (pH: 1.9) | 5.7 | 4.6 | | | | | | |
| 10 | 1.0% $H_2O_2$ + 4% SA + 0.6% Bardac 22 + 0.10% EDDS (pH: 2.9) | 5.9 | 4.52 | | | | | | |
| 11 | 1.0% $H_2O_2$ + 4% CA + 0.6% Bardac 22 + 0.10% EDDS (pH: 2.5) | 5.86 | 5.44 | 5.86 | 5.6 | | | | |

PA = phosphoric acid;
HEDP = edidronic acid;
CA = citric acid;
SA: succinic acid;
Bardac 22 = Didecyldimethylammonium chloride;
EDDS: S,S-ethylenediamine-N,N'-disuccinic acid trisodium salt.

Furthermore, the results demonstrate that the composition comprising 0.5% hydrogen peroxide, 2% citric acid, 0.3% Bardac 22 and 0.05% EDDS shows excellent activity with 4.6 Log reduction against *Mycobacterium terrae* ATCC 15755 within 5 minutes of contact time, determined by OECD Quantitative methods for Evaluating the activity of Mycobactericidal used on hard Non-Porous Surfaces (Draft 30 Oct. 2012).

Example 2: Biocidal Activities Against *Bacillus subtillis*

Biocidal activities of the exemplified compositions were determined using OECD Quantitative Suspension Test for the Evaluation of Sporicidal Activity of Chemical Disinfectants used in Food, Industrial; Domestic and institutional areas. Neutralization was performed by membrane filtration using D/E Broth with 1% catalase as rinse fluid. The test was performed at 20° C. for 60 minutes, using 0.3 g/l bovine albumin as the interfering substance.

The following raw materials were used: 50% hydrogen peroxide, citric acid (CA), lactic acid, 50% 1-hydroxyethane 1,1-diphosphonic acid (HEDP), sodium stannate, dipicolinic acid (DPA) STEPANETEX® DA-6, DOWANOL™ DPnP, sodium hydroxide (NaOH), methanesulfonic acid (MSA), NOVEL® 1012-6 ethoxylate, bovine albumin, isopropanol, D/E broth, and catalase. Bardac 2250, containing of 50%

TABLE 3

| Formulation (100% balanced with D.I. water) | #Log against *Bacillus subtillis* within 60 sec contact time |
|---|---|
| 2.0% $H_2O_2$ + 4.0% CA + 0.6% Bardac 22 + 4.0% MSA + 1.6% Stepanetex ® DA-6 + 2.0% Dowanol DPnP + 0.10% HEDP + 0.8% NaOH (pH ~1.20) | 3.30 |
| 2.0% $H_2O_2$ + 4% Lactic acid + 0.6% Bardac 22 + 0.5% MSA + 1.6% Novel ® 1012-6 ethoxylate + 2.0% isopropanol + 0.10% HEDP (pH ~1.76) | 4.68 |

These results demonstrate that the compositions comprising an alcoholic solvent displayed effective antimicrobial activity against *Bacillus subtillis*.

Furthermore, the results demonstrate that the composition comprising 2.0% hydrogen peroxide, 4.0% lactic acid, 0.6% Bardac 22, 0.5% MSA, 1.6% 1012-6 ethoxylate, 2.0% isopropanol, and 0.10% HEDP (pH~1.76) shows excellent activity with 4.7 Log reduction against *Bacillus subtillis* ATCC 6633 (Spores) within 60 seconds of contact time.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type

What is claimed is:

1. A disinfectant composition comprising a biocidal quaternary ammonium compound, hydrogen peroxide, and at least one acid or salt thereof, wherein the quaternary ammonium compound is a compound having the formula (I):

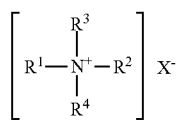

(Formula I)

wherein $R^1$ is an optionally substituted benzyl group or an optionally substituted alkyl or aryl-substituted alkyl group;

$R^2$ and $R^3$ are independently optionally substituted alkyl groups;

$R^4$ is selected from the group consisting of an optionally substituted alkyl or aryl-substituted alkyl group, benzyl group, and $[(CH_2)_2—O]_n—R^5$, wherein n is an integer from 1 to 20 and $R^5$ is selected from the group consisting of hydrogen, phenyl, and alkyl-substituted phenyl; and $X^-$ is chlorine, bromine, phosphate, sulfate, or nitrate; and wherein the composition is a dilutable composition comprising 0.5 to 5% by weight of the quaternary ammonium compound, 0.5 to 25% by weight hydrogen peroxide, and 1-25% by weight of the at least one acid or salts thereof and wherein the composition is free of peracids.

2. A separate two-part disinfectant composition, wherein a first part of the composition comprises a biocidal quaternary ammonium compound and at least one acid or salt thereof, and wherein a second part of the composition comprises hydrogen peroxide, wherein the quaternary ammonium compound is a compound having the formula (I):

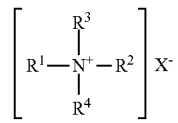

(Formula I)

wherein $R^1$ is an optionally substituted benzyl group or an optionally substituted alkyl or aryl-substituted alkyl group;

$R^2$ and $R^3$ are independently optionally substituted alkyl groups;

$R^4$ is selected from the group consisting of an optionally substituted alkyl or aryl-substituted alkyl group, benzyl group, and $[(CH_2)_2—O]_n—R^5$, wherein n is an integer from 1 to 20 and $R^5$ is selected from the group consisting of hydrogen, phenyl, and alkyl-substituted phenyl; and $X^-$ is chlorine, bromine, phosphate, sulfate, or nitrate; and wherein the composition is a dilutable composition comprising 0.5 to 5% by weight quaternary ammonium compound, 0.5 to 25% by weight hydrogen peroxide, and 1-25% by weight the acid or salt thereof, and wherein the composition is free of peracids.

3. The composition according to claim 1, wherein $R^1$ and $R^4$ are $C_{1-22}$ alkyl.

4. The composition according to claim 1, wherein $R^2$ and $R^3$ are $C_1$-$C_4$ alkyl.

5. The composition according to claim 1, wherein $R^1$ and $R^4$ are $C_{1-22}$ alkyl, and $R^2$ and $R^3$ are methyl.

6. The composition according to claim 1, wherein the quaternary ammonium compound comprises didecyl dimethyl ammonium chloride and/or $C_8$-$C_{18}$ alkyldimethylbenzylammonium chloride.

7. The composition according to claim 1, wherein the acid is in the form of an alkaline metal salt of the acid.

8. A method of killing or inhibiting growth of microorganisms on a surface comprising diluting the composition according to claim 1 with water, and then applying the diluted composition to a surface.

9. The composition according to claim 1, wherein the composition is a dilutable composition comprising 2-5% by weight quaternary ammonium compound, 3-8% by weight hydrogen peroxide, and 1-5% by weight the acid or salt thereof.

10. A disinfectant composition comprising a biocidal quaternary ammonium compound, hydrogen peroxide, and at least one acid or salt thereof, wherein the quaternary ammonium compound is a compound having the formula (I):

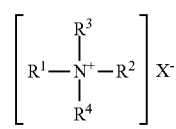

(Formula I)

wherein $R^1$ is an optionally substituted benzyl group or an optionally substituted alkyl or aryl-substituted alkyl group;

$R^2$ and $R^3$ are independently optionally substituted alkyl groups;

$R^4$ is selected from the group consisting of an optionally substituted alkyl or aryl-substituted alkyl group, benzyl group, and $—[(CH_2)_2—O]_n—R^5$, wherein n is an integer from 1 to 20 and $R^5$ is selected from the group consisting of hydrogen, phenyl, and alkyl-substituted phenyl; and $X^-$ is chlorine, bromine, phosphate, sulfate, or nitrate; wherein the composition is a ready to use composition comprising 0.01-1.5% by weight quaternary ammonium compound, 0.1-1.5% by weight hydrogen peroxide, and 0.5 to 4% by weight acid, and wherein the composition is free of peracids.

11. The composition according to claim 1, further comprising a stabilizer, solvent, or additive.

12. The composition according to claim 11, wherein the solvent is present and selected from the group consisting of:

water, ethanol, propanol, isopropanol, propylene glycol, dipropylene glycol n-propyl ether, and dipropylene glycol methyl ether.

13. The composition according to claim 1, further comprising a chelant and/or a corrosion inhibitor.

14. A method of killing or inhibiting growth of microorganisms on a surface comprising applying the composition of claim 1 to a surface.

15. The method according to claim 14, wherein the microorganisms comprise one or more of Gram positive bacteria, Gram negative bacteria, viruses, fungi, mildew, or mold.

16. The method according to claim 14, wherein the microorganisms comprise one or more of *Staphylococcus, Pseudomonas, Bacillus*, hepatitis, rotavirus, rhinovirus, or *Mycobacterium terrae*.

17. The composition according to claim 1, comprising at least two acids or salts thereof selected from the group consisting of citric acid, phosphoric acid, glutaric acid, succinic acid, lactic acid, S,S-ethylenediamine-N,N'-disuccinic acid, 1-hydroxyethane 1,1-diphosphonic acid (HEDP), dipicolinic acid (DPA), methanesulfonic acid (MSA), acetic acid, tartaric acid, adipic acid, oxalic acid, sulfamic acid, benzoic acid, formic acid, glycolic acid, polymeric acid, phytic acid, phosphoacetic acid, diethylenetriaminepentakis (methylphosphonoic acid), and N-(phosphonomethyl)iminodiacetic acid, or salts thereof.

18. The method according to claim 14, wherein the composition demonstrates a minimum of 5 log reduction of microorganisms within about 5 minutes of contact time with the microorganisms.

19. The composition according to claim 17, wherein the at least two acids or salt thereof comprise at least one acid selected from the group consisting of citric acid, succinic acid, phosphoric acid, glutaric acid, dipicolinic acid (DPA), and lactic acid in combination with at least one acid selected from the group consisting of S,S-ethylenediamine-N,N'-disuccinic acid or its alkaline salt, 1-hydroxyethane 1,1-diphosphonic acid (HEDP), and methanesulfonic acid (MSA).

20. The composition according to claim 1, wherein there are at least two acids, and the acids are selected from the group consisting of citric acid, phosphoric acid, succinic acid, glutaric acid, dipicolinic acid (DPA), lactic acid, S,S-ethylenediamine-N,N'-disuccinic acid or its alkaline salt, 1-hydroxyethane 1,1-diphosphonic acid (HEDP), and methanesulfonic acid (MSA).

21. The composition according to claim 1, wherein the at least one acid or salt thereof is selected from the group consisting of citric acid, phosphoric acid, glutaric acid, succinic acid, lactic acid, S,S-ethylenediamine-N,N'-disuccinic acid, 1-hydroxyethane 1,1-diphosphonic acid (HEDP), dipicolinic acid (DPA), methanesulfonic acid (MSA), acetic acid, tartaric acid, adipic acid, oxalic acid, sulfamic acid, benzoic acid, formic acid, glycolic acid, polymeric acid, phytic acid, phosphoacetic acid, diethylenetriaminepentakis (methylphosphonoic acid), and N-(phosphonomethyl)iminodiacetic acid, or salt thereof.

* * * * *